US007090497B1

(12) United States Patent  
Harris

(10) Patent No.: US 7,090,497 B1  
(45) Date of Patent: Aug. 15, 2006

(54) METHOD OF PERIODONTAL LASER TREATMENT

(76) Inventor: David M. Harris, 4256 Heyer Ave., Castro Valley, CA (US) 94546

( * ) Notice: Subject to any disclaimer, the term of this patent is extended or adjusted under 35 U.S.C. 154(b) by 62 days.

(21) Appl. No.: 10/066,162

(22) Filed: Jan. 31, 2002

Related U.S. Application Data

(60) Provisional application No. 60/270,958, filed on Feb. 21, 2001.

(51) Int. Cl.  
*A61C 5/00* (2006.01)

(52) U.S. Cl. ...................... 433/215; 433/216

(58) Field of Classification Search ............ 433/215–6, 433/216, 29; 606/2–16; 607/88, 89, 92, 607/93; 424/49  
See application file for complete search history.

(56) References Cited

U.S. PATENT DOCUMENTS

| | | | |
|---|---|---|---|
| 4,764,114 A | 8/1988 | Jeffcoat et al. ............... 433/72 |
| 4,877,401 A | 10/1989 | Higuchi et al. ............. 433/215 |
| 5,055,048 A | 10/1991 | Vassiliadis et al. ......... 433/215 |
| 5,090,908 A | 2/1992 | Teumim-Stone ............ 433/215 |
| 5,171,148 A | 12/1992 | Wasserman et al. ........ 433/215 |
| 5,194,005 A | 3/1993 | Levy .......................... 433/215 |
| 5,230,621 A | 7/1993 | Jacoby ........................ 433/29 |
| 5,328,365 A | 7/1994 | Jacoby ........................ 433/29 |
| 5,342,198 A | 8/1994 | Vassiliadis et al. ......... 433/215 |
| 5,374,266 A | 12/1994 | Kataoka et al. ............. 606/15 |
| 5,401,171 A | 3/1995 | Paghdiwala ................ 433/215 |
| 5,435,724 A | 7/1995 | Goodman et al. .......... 433/215 |
| 5,456,603 A | 10/1995 | Kowalyk et al. ........... 433/215 |
| 5,549,596 A | 8/1996 | Latina .......................... 606/4 |
| 5,595,568 A | 1/1997 | Anderson et al. ............. 606/9 |
| 5,611,793 A | 3/1997 | Wilson et al. ................. 606/2 |
| 5,616,140 A | 4/1997 | Prescott ....................... 606/10 |
| 5,616,141 A | 4/1997 | Cipolla ........................ 606/15 |
| 5,631,228 A | 5/1997 | Oppenheim et al. .......... 514/12 |
| 5,642,997 A | 7/1997 | Gregg, II et al. ........... 433/215 |
| 5,646,119 A | 7/1997 | Oppenheim et al. .......... 514/12 |
| 5,658,148 A | 8/1997 | Neuberger et al. .......... 433/215 |
| 5,759,200 A | 6/1998 | Azar ........................... 607/89 |
| 5,766,214 A | 6/1998 | Mehl, Sr. et al. ............. 606/9 |
| 5,795,153 A * | 8/1998 | Rechmann .................. 433/216 |
| 5,836,999 A | 11/1998 | Eckhouse et al. ............ 607/88 |
| 5,885,082 A | 3/1999 | Levy .......................... 433/215 |
| 5,885,965 A | 3/1999 | Oppenheim et al. .......... 514/12 |
| 5,897,509 A | 4/1999 | Toda et al. ................. 600/589 |
| 5,912,230 A | 6/1999 | Oppenheim et al. .......... 514/12 |
| 5,915,161 A | 6/1999 | Adams .................... 422/186.3 |
| 6,019,605 A * | 2/2000 | Myers ........................ 433/215 |
| 6,044,514 A | 4/2000 | Kaneda et al. ............. 15/167.1 |
| 6,088,869 A | 7/2000 | Kaneda et al. ............. 15/167.1 |
| 6,129,721 A | 10/2000 | Kataoka et al. ............... 606/2 |

(Continued)

*Primary Examiner*—Linda C. M. Dvorak  
*Assistant Examiner*—Aaron Roane  
(74) *Attorney, Agent, or Firm*—Haverstock & Owens LLP

(57) ABSTRACT

A method of selectively treating microbiological pathogens which are implicated in the advancement of periodontitis is disclosed. Preferably, the microbiological pathogens are phorphyromonas gingivalis (Pg) and prevotella intermedia (Pi) which are known to colonize in dental plaque, cementum, gingival sulcus epithelium and surrounding periodontal tissues. The microbiological pathogens can also include pigmented fungi such as Histoplasma and Aspirgillus Niger. The microbiological pathogens are selectively irradiated with high-energy antiseptic laser pulses which are strongly absorbed by the microbiological pathogens and which are substantially transparent to the periodontal tissues. Preferably, high-energy antiseptic laser pulses eradicate a portion of the microbiological pathogens within the periodontal tissues without requiring aggressive debridement procedures.

30 Claims, 7 Drawing Sheets

U.S. PATENT DOCUMENTS

| | | | |
|---|---|---|---|
| 6,153,210 A | 11/2000 | Roberts et al. | 424/411 |
| 6,179,830 B1 | 1/2001 | Kokubu | 606/16 |
| 6,267,771 B1 | 7/2001 | Tankovich et al. | 606/131 |
| 6,462,070 B1 * | 10/2002 | Hasan et al. | 514/410 |
| 6,506,563 B1 * | 1/2003 | Ward et al. | 435/6 |

* cited by examiner

METHOD OF PERIODONTAL LASER TREATMENT

RELATED APPLICATIONS

This patent application claims priority under 35 U.S.C. 119 (e) of the co-pending U.S. Provisional Patent Application Ser. No. 60/270,958, filed Feb. 21, 2001, and entitled "A METHOD AND DEVICE THAT WILL SELECTIVELY COAGULATE MICROBIOLOGICAL PATHOGENS". The Provisional Patent Application Ser. No. 60/270,958, filed Feb. 21, 2001, and entitled "A METHOD AND DEVICE THAT WILL SELECTIVELY COAGULATE MICROBIOLOGICAL PATHOGENS" is also hereby incorporated by reference.

FIELD OF THE INVENTION

The present invention relates to methods of selectively treating microbiological pathogens with radiation. More specifically, this invention relates to methods of treating microbiological pathogens within an oral cavity to reduce the advancement of periodontal disease.

BACKGROUND OF THE INVENTION

Gum disease, or periodontal disease, is commonly associated with the presence of bacterial pathogens within periodontal pockets between the dentin and gum tissue. Gingivitis describes a periodontal condition of inflammation within the superficial layers of the periodontium. Periodontitis is advanced Gingivitis, whereby the inflammation is extended to the underlying tooth supporting structures and other deep periodontal tissues. Attachment loss and gum recession is symptomatic of advance gingivitis or periodontitis which can leave extremely sensitive portions of underlying tooth supporting structures exposed.

Ultimately, periodontitis leads to the destruction of both supra-alveolar and periodontal fibers as well as the adjacent portion of the alveolar bone which generally provides for the attachment of healthy soft periodontal tissue to the cementum. When the soft periodontal tissue becomes inflamed as a result of bacteria, the edematous and junctional epithelium recedes away from the cementum creating an enlarged periodontal pocket and attachment loss of the soft periodontal tissue to the cementum.

Enlarged periodontal pockets provide collection sites for plaque and calculus which adheres to root surfaces. Calcified plaque and calculus provide rough surfaces which are a highly suitable environment for hosting and colonizing bacterial pathogens. One category of bacterial pathogens which has been strongly implicated in the progression of periodontal disease are referred to as gram (-) anaerobic pathogenic bacteria.

Periodontal bacteria have been shown to migrate into surrounding soft tissues and survive within endothelial cells, macrophage and perivascular cells. Periodontal bacteria can also survive in hard periodontal tissue including dentin, bone and cementum tissue. Periodontal bacteria can also enter into the general circulation system through various systemic routes and mechanisms.

Periodontal disease has been correlated to several systemic conditions, such as cardiovascular disease, and is thought to contribute to other heath problems including pre-term delivery and low infant birth weight for infants delivered from mothers having periodontal disease. While there is no comprehensive list of health related problems associated with periodontal disease nor is there a complete understanding as to whether periodontal disease is aggravated by other health conditions or vise-versa, it is commonly believed that periodontal disease can propose a health risk.

The most effective therapy for gum disease is to motivate patients to improve their personal oral hygiene habits. Unfortunately, attachment loss is a progressive condition due to the activation mechanisms of collagen destruction and bone resorption. Therefore, adhering to a aggressive maintenance regimen will not typically improve the gum recession. However, gum recession can be stopped, or at least the rate of gum recession can be significantly reduced.

Topological antibiotic therapies are usually ineffective in the eradication of periodontal bacteria because a portion of the bacteria which survive such therapies and can re-colonize. Bacteria survive topological antibiotic therapies by virtue of being isolated deep within dental calculus and/or intracellular locations of periodontal tissues and are, therefore, topologically privileged. Systemic antibiotic therapies are also typically ineffective in the eradication of periodontal bacteria because dental calculus and intracellular locations are also systemically privileged and not accessible by the host's circulation system. Besides being ineffective, antibiotic therapies can lysis non-privileged bacteria causing fragments of the bacteria to enter the blood stream and result in "endotoxic shock" or "septic shock" to the patient.

Because of the numerous shortcomings of antibiotic therapies, mechanical methods are usually employed, either solely or in combination with antibiotic therapies. Mechanical procedures, also referred to herein as debridement, include removing calculus, diseased cementum and/or necrotic soft tissue within the gingival sulcus containing the bacteria. These procedures are more commonly referred to as scaling, root planing and sulcular debridement. In debridement procedures, a curette, ultrasonic scalar or any other suitable device is used to remove infected or diseased tissue from healthy tissue with the intent of reestablishing attachment of the remaining healthy soft periodontal tissue.

There are even more aggressive treatments for patients with highly advanced periodontitis. In these more aggressive treatments flaps from the gum tissue are cut and removed or pulled away from the root structures in order to access the root surface so that the diseased tissues can be removed. After the diseased tissues are removed, the gingival flaps are sutured back into place. Grafting procedures are also frequently used to "build-up critical tissues" around dentition, wherein the critical tissues have been depleted from periodontitis or treatments thereof.

In addition to the obvious discomfort suffered to the patient during and after these aggressive mechanical treatments, such mechanical treatments also have several shortcomings. Mechanical treatments are not a cure for periodontitis because pathogen may survive within the periodontal tissues. Even a small amount of living bacteria within the soft tissues, hard tissues or semi-hard tissues can allow the bacteria to re-colonize quickly after the treatment. Mechanical treatments can result in the systemic release of toxic bacteria fragments leading to toxic shock and possible other health problems. Also, mechanical treatments can only be implemented a limited number of times without requiring oral surgery and/or grafting of gum tissues. Some patients are, unfortunately, highly susceptible to periodontal disease and debridement is not a viable long term solution to prevent the advancement of attachment loss of the soft periodontal tissue to the cementum.

What is needed is a system for and method of treating pathogens within an oral cavity. Further, what is needed is periodontal treatment which can be used to treat periodontal tissues in the early phases of periodontal disease and which can be administered multiple times without causing serious trauma to gum tissue and without causing significant systemic release of toxins from treated pathogens.

SUMMARY OF THE INVENTION

The current invention provides a system for and method of generating at least one antiseptic pulse to a target area of a target tissue. The target tissue is preferably a periodontal tissue. The antiseptic pulse is preferably a high-energy pulse of laser light which is preferentially absorbed by one or more target pathogens. The high-energy pulse of laser light preferably penetrates into the target periodontal tissue to a distance of 1.0 mm or greater and eradicates the target pathogens, or a portion thereof, within the target tissue. The depth to which the pathogens are eradicated is referred to, herein, as the effective treatment depth. The effective treatment depth multiplied by the target area exposed by each laser pulse is referred to, herein, as the effective treatment volume. The method of the instant invention preferably utilizes laser pulses which denature or coagulate the target pathogens within the effective treatment volume and is, therefore, coined as photo-thermo-coagulation.

Unlike with antibiotic therapies, periodontal bacteria will not likely develop resistance to photo-thermo-coagulation. Further, because periodontal tissues are substantially transparent to the laser radiation used, the treatment can be administered a number of times without significantly effecting healthy periodontal tissues. Also, it is believed that photo-thermo-coagulation does not result in significant systemic release of toxins. The periodontal laser treatment, described below, can be used in conjunction with debridement procedures and antibiotic therapies. However, the periodontal laser treatment of the instant invention is preferably used in place of aggressive mechanical treatments.

The target pathogens can be any number of pathogens that selectively absorb the laser pulses used, and which preferably are implicated in periodontal disease. Bacteria which are known to cause periodontal disease, include but are not limited to, pigmented gram (-) anaerobes such as phorphyromonas gingivalis (Pg) and prevotella intermedia (Pi). The current invention can also be used to treat pigmented fungus such as Histoplasma and Aspirgillus Niger.

In accordance with the method of the instant invention, the target pathogens are preferably located within the oral cavity. In advanced gingivitis, observation of the soft periodontal tissue may be sufficient to diagnose for the presence and the location of the target pathogens. In early stages of periodontal disease, however, a culture or the use of other analytical techniques (such as a DNA testing) may be required to identify or locate the target pathogens.

The periodontal laser treatment may be tailored to a specific target pathogen by spectroscopically characterizing the specific target pathogen and selecting a laser treatment wavelength corresponding to a larger absorption coefficient for the specific target pathogen. Preferably, the absorption coefficient of the specific target pathogen is at least ten times greater than the absorption coefficient of normal or healthy periodontal tissue.

After the pathogen has been located and/or characterized within the oral cavity, an area of target tissue is irradiated with at least one pulse of laser light. In accordance with an embodiment of the instant invention, the target tissue is soft periodontal tissue surrounding a periodontal pocket. In further embodiments of the instant invention, the target tissue comprises cementum, dentin and or infected bone. Accordingly, the pulse of laser light can be delivered external to the periodontal pocket or from within the periodontal pocket by placing a firing end of an optical fiber near the target tissue and pulsing laser light through the optical fiber.

The pathogen is preferably irradiated with one or more pulses of laser light each having sufficient energy to eradicate the target pathogen, or a portion thereof, within the effective treatment volume. The laser treatment is preferably 1.0 second, or less, of laser radiation to each target area treated. When the target area is outer soft periodontal tissue, the laser radiation preferably, penetrates a distance of 1.0 mm or greater into the soft periodontal tissue. More preferably, the laser radiation penetrates 2.0 mm or greater into the soft periodontal tissue, such that a portion of the pathogens within the periodontal pocket and the inner pocket tissues are eradicated without requiring mechanical displacement of the patient's gums.

When the laser source is a Nd:YAG laser source, laser pulses preferably have energy concentrations of 10 $J/cm^2$ or greater within the tissue(s) at the site of pathogen eradication. However, the specific dosimetry that is chosen is dependent on the optical properties of the irradiated tissue(s) including, but not limited to, transmission through non-target tissues and absorption coefficients of target tissues at the light source wavelength. Preferably, laser radiation is delivered to each area treated with a laser fluence of 350 $Joule/cm^2$ or greater and total laser energy of 2 Joules or more, in order to ensure that target pathogens within the effective treatment volume are eradicated.

Prior to treating target pathogens with pulsed laser light, the pathogens can be stained with a staining agent or a pigment to facilitate the absorption of the laser light. Also, prior to the laser treatment or, alternatively, after the laser treatment, the pathogens can be stained with a staining agent which stains for the presence of living bacteria. The periodontal laser treatment can be administered any number or times as required to eradicate the bacteria or until the observed concentrations of the living bacteria are at prescribed levels.

A laser system in accordance with the instant invention, is configured to deliver pulses of laser radiation to target periodontal tissues within an oral cavity. The laser system comprises a laser source, that is preferably a pulsed laser source, for generating pulsed laser light having a peak wavelength in a range of 600 to 1100 nanometers. The system preferably includes a delivery system with an arm structure and an applicator.

The delivery system is configured with any suitable optics for delivering the laser light from the laser source to the target tissues. Suitable optics include, but are not limited to lenses, mirrors, optical fibers and scanning mirrors. Preferably, the delivery system is configured to deliver pulsed laser light to a wide field exposure area. The wide field exposure area preferably corresponds to a surface area of 1.0 to 9 $mm^2$ or more.

In accordance with an embodiment of the invention, the applicator includes a side-firing optical fiber configured to emit pulsed laser light at an angle from the firing end of the optical fiber. The applicator can also be configured with a soft resilient guide member for controlling the distance between the laser light emitted from the firing end of the optical fiber and the target tissue.

DETAILED DESCRIPTION OF A PREFERRED EMBODIMENT

Figure 1:
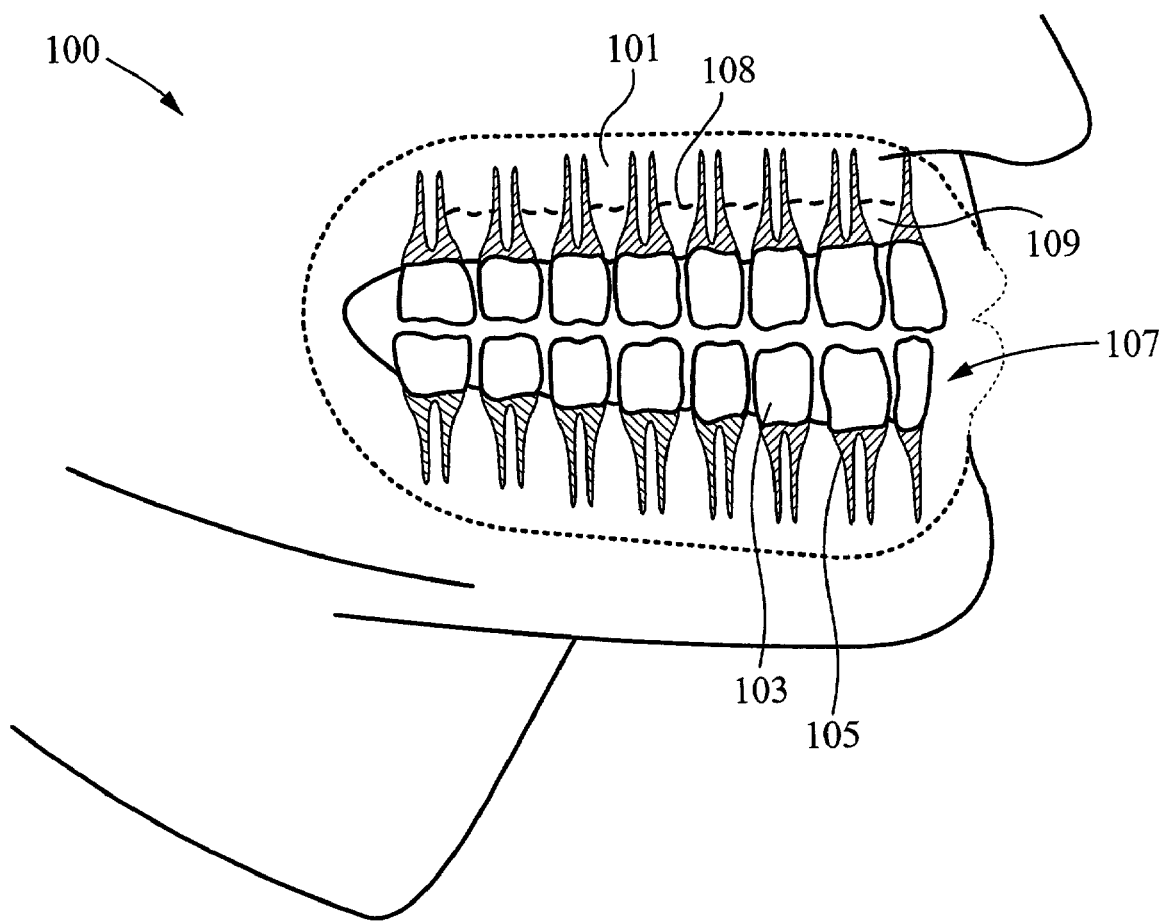
FIG. 1 illustrates a schematic representation of human dentition.

FIG. 1 illustrates a schematic representation of human dentition 100. Teeth 103 in an oral cavity 107 are embedded within surrounding periodontal tissue 101. The teeth 103 are attached to a jaw bone (not shown) through root structures 105. In advanced cases of periodontal disease, the periodontal tissue 101 detaches from portions of the root structures 105, as indicated by the dotted lines 108, thereby forming periodontal pockets and/or exposing sensitive portions 109 of the root structures 105. Late stages of periodontal disease and result in the complete detachment of the periodontal tissue 101 from the underlying root structures 105 and ultimately result in the loss of teeth 103, as described below.

Figure 2A:
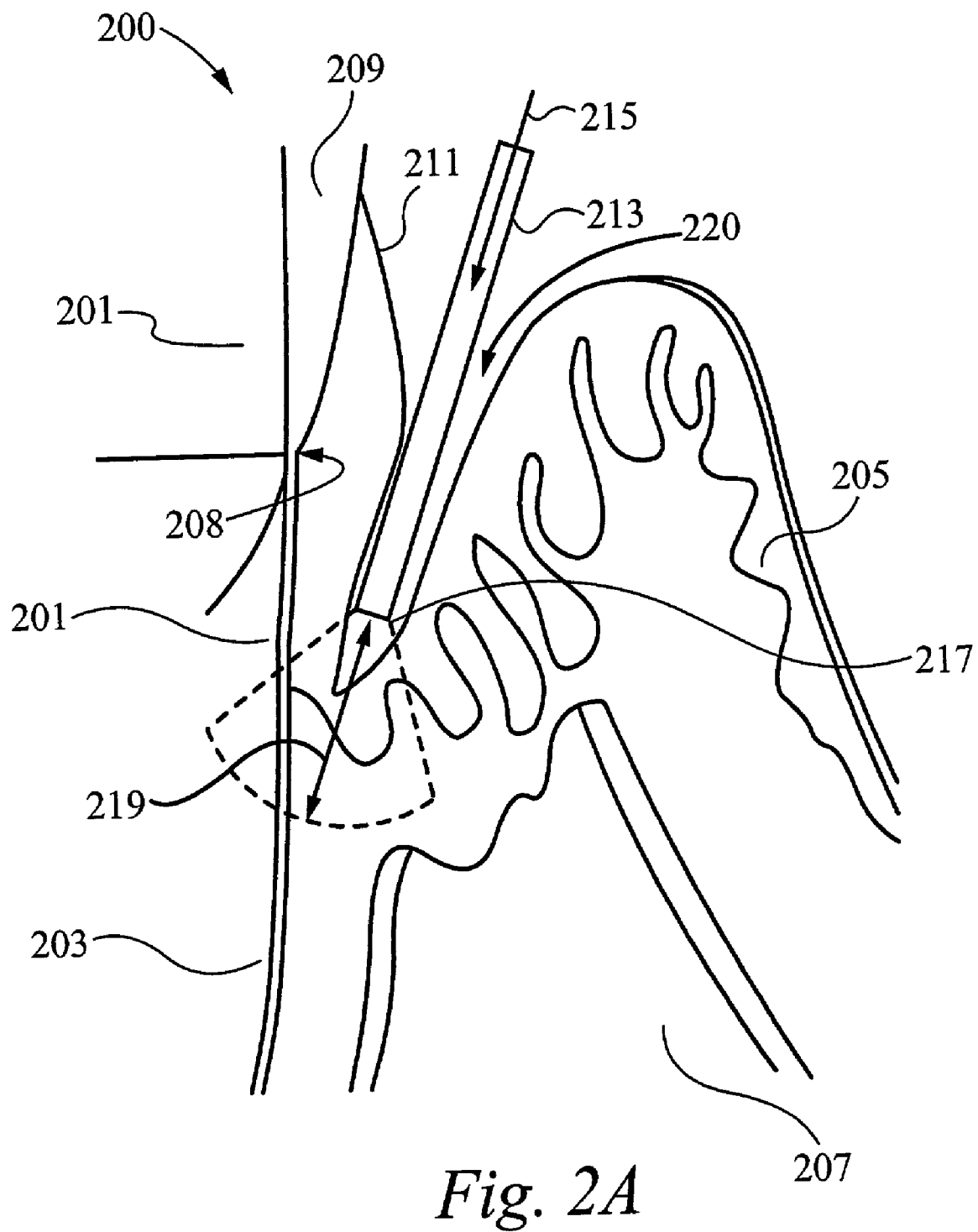
FIG. 2A illustrates a cross-section of a periodontal pocket and a method of applying laser radiation to periodontal tissues from within the periodontal pocket, in accordance with the current invention.

FIG. 2A shows a cross-sectional view 200 of a periodontal pocket 220 and surrounding periodontal tissues. With periodontal disease, the soft periodontal tissue 205 become detached or separated from the cementum 203, which is a layer of hard tissue on the outer surface of the root. Below the cementum 203 is the dentin 201. Normally, the periodontal ligament(s) attach up to cemento-enamel junction 208. As periodontal disease progresses, this attachment level recedes apically (toward the root). The ultimate result can be loss of attachment to the bone 207 and loss of the tooth.

When the soft periodontal tissue 205 remains above the point of attachment, then a periodontal pocket 220 is formed. For example, the attachment loss, as measured from the cemento-junction 208 is 8.0 mm. If the soft periodontal tissue 205 has receded apically by 3.0 mm, then the depth of the periodontal pocket 220 is 5.0 mm.

The calculus 211 and plaque within the periodontal pocket 220 are, unfortunately, excellent hosts for bacterial growth which can lead to advanced periodontal disease, as described above. The bacteria which is colonized within the periodontal pocket 220 can penetrate surrounding periodontal tissues and occupy intercellular positions within the soft periodontal tissues 205, the bone tissue 207 and the cementum 203 making topological or systemic antibiotic therapies ineffective for the eradication of the bacteria and/or fungus.

Accordingly, the current invention seeks to eradicate such pathogens within the periodontal pocket 220 and within the surrounding tissues by providing an antiseptic laser pulse or sequence of antiseptic laser pulses having a wavelength in the range of 600 to 1100 manometers. The laser pulses are generated from any suitable laser source including a Nd:YAG laser source, a solid-state laser diode, a gas laser source or combinations thereof. The laser radiation from the laser pulses, preferably penetrate the soft periodontal tissue 205 by a distance 219 of at least 1.0 mm and more preferably by a distance 219 of at least 2.0 mm.

The laser treatment can be less than 1.0 second for each area treated, but preferably each area treated is exposed to laser radiation with energy concentrations of at least 17.0 $J/cm^2$, a laser fluence of at least 350 $Joule/cm^2$ and total energy of at least 2 Joules in order to ensure that target pathogens within the effective treatment volume are eradicated.

Still referring to FIG. 2A, in order to administer the laser radiation 215 to the target tissue, an optical fiber 213 is inserted in the periodontal pocket 220. The laser radiation 215 is delivered through the firing end 217 of the optical fiber 213. The optical fiber 213 can be moved up and down or side-to-side within the periodontal pocket 220 to ensure that the entire periodontal pocket 200 is treated with the laser radiation.

Figure 2B:
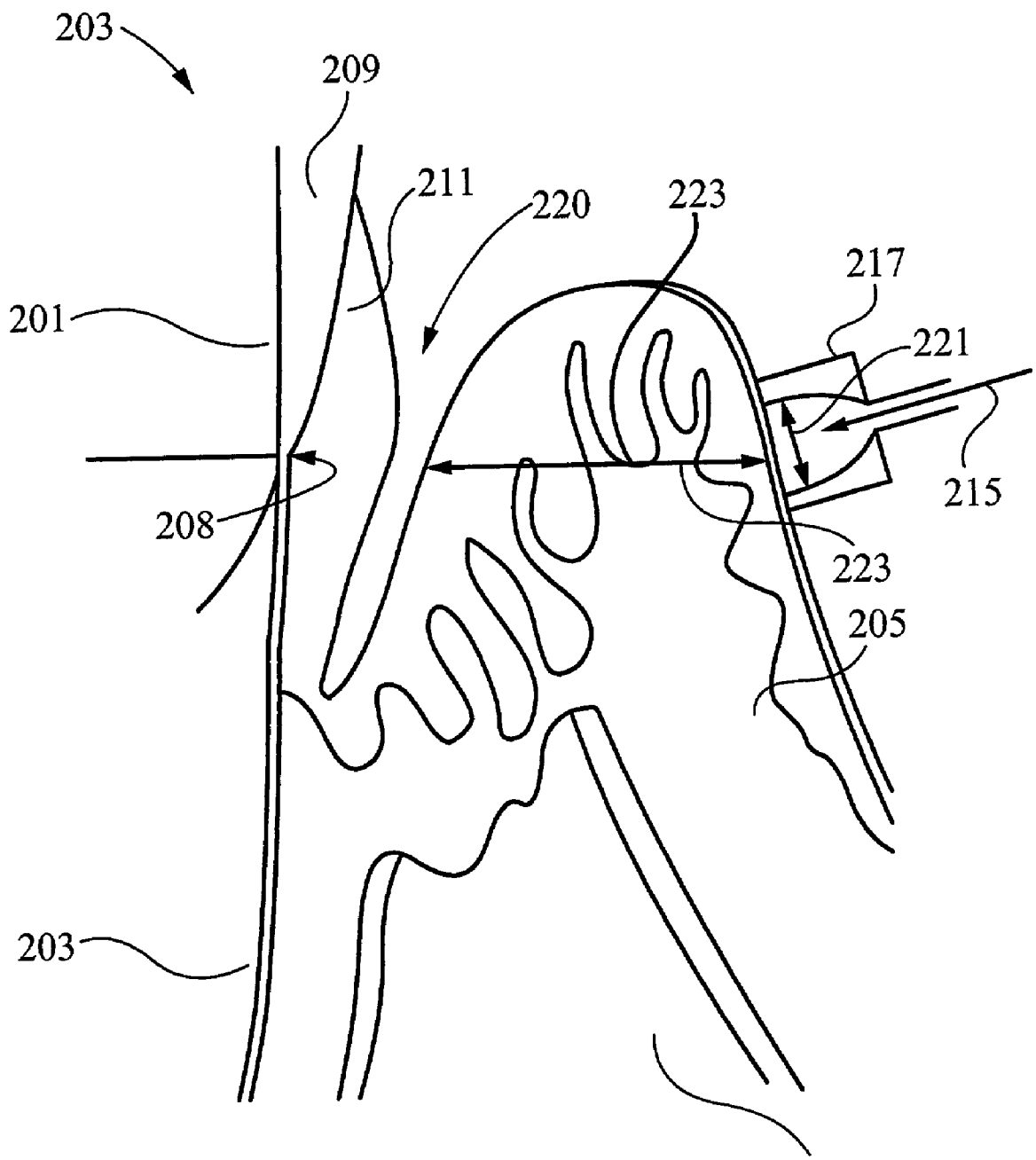
FIG. 2B illustrates a cross-section of a periodontal pocket and methods of applying laser radiation to the periodontal pocket through tissues outside of the periodontal pocket, in accordance with the current invention.

FIG. 2B illustrates a cross-section 203 of the periodontal pocket 220 along with the surrounding dentin 201, cementum 203, bone 207, enamel 209 and soft periodontal tissue 205. Again, the soft periodontal tissue 205 is slightly separated from the cementum 203 and/or dentin 201 as a result of infectious bacteria colonized on or within the calculus 211, calcified plaque and/or surrounding tissues.

In accordance with the instant invention, laser radiation is delivered to a target tissue with penetration depth of 2.0 cm and less, wherein the surface is treated with antiseptic laser pulses as well as the tissue(s) below the surface. Soft periodontal tissues, hard periodontal tissues and plaque can be treated in accordance with the instant invention to photocoagulate host pathogens In accordance with an alternative embodiment of the invention, laser radiation 215 is delivered from a laser applicator to outer portions of the soft periodontal tissue 205. Accordingly, the laser applicator 217 is placed onto or next to the outer portions of the soft periodontal tissues 205 and at least one antiseptic laser pulse is delivered to the target area of the soft periodontal tissue 205. Preferably, the target area is a wide field exposure area 217 corresponding to a surface area of 1.0 to 9 $mm^2$, or greater. The laser radiation 215, or a portion thereof, preferably penetrates to a depth 223 of 2.0 cm or less through soft periodontal tissue 205, dentin 201, cementum 203 bone tissue 207 or any other infected tissue, such that at least a portion of the target pathogens within the periodontal pocket 220 and or/within the target tissues are eradicated. Preferably, the laser treatment also effectively eradicates both intra- and extra-cellular pathogens within the irradiated sort tissue 205, hard tissues 201, 203 and 207 and/or the plaque In a preferred embodiment the dosimetry of the laser treatment corresponds to an effective treatment volume of laser pulses, wherein the pathogen within the treatment volume of the are substantially irradiated.

The larger field exposure area 211 can be irradiated through an optical fiber, a focusing lens, a bundle optical fibers or any combination thereof. Alternatively, a large field exposure area 211 is irradiated by a laser scanner which either rasters the laser beam 215 over the target area or, alternatively, projects a series of closely spaced or overlapping spots onto the target area.

Figure 3:
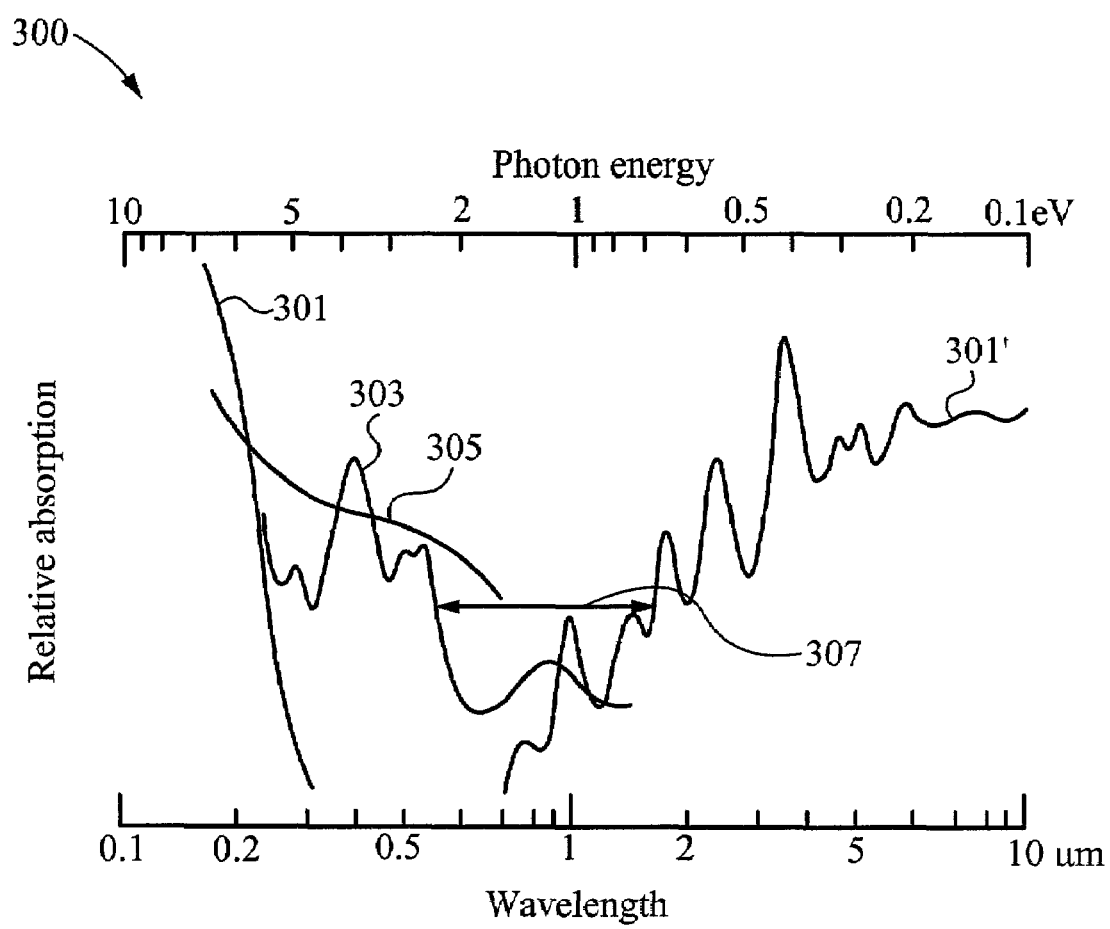
FIG. 3 shows absorption spectra of water, hemoglobin, and melanin between 0.1 and 10 micron wavelength light.

FIG. 3 shows absorption spectra 300 for water, hemoglobin and melanin, which are major contributors to the absorption of light in periodontal tissues. The lines 301 and 301' in the graph of FIG. 3 correspond to the absorption of water, the line 303 corresponds to the absorption of hemoglobin and the line 305 corresponds to the absorption of melanin for light having wavelengths between 100 to 10,000 nanometers. The absorption spectra 300 shows that there is a preferred window of wavelengths 307 which are essentially non-absorbing water, hemoglobin and melanin corresponding approximately to light having wavelengths between 550 to 1800 nanometers.

In developing a selective treatment for a target pathogen or target pathogens, the target pathogens are isolated from target tissues. The pathogens are then preferably characterized by collecting absorption spectra for one or more of the target pathogens within the preferred wavelength window 307. After the pathogens have been-spectroscopically characterized within the preferred wavelength window 307, then a laser treatment wavelength is selected which corresponds approximately to an absorption peak of at least one of the target pathogens. When a mixture of pathogens is present, the laser treatment wavelength can be chosen such as to maximize the collective absorptions of each pathogen within the mixture of target pathogens. Alternatively, different treatment procedures can be developed for each pathogen or for a selected group of pathogens within the mixture of target pathogens.

Figure 4:
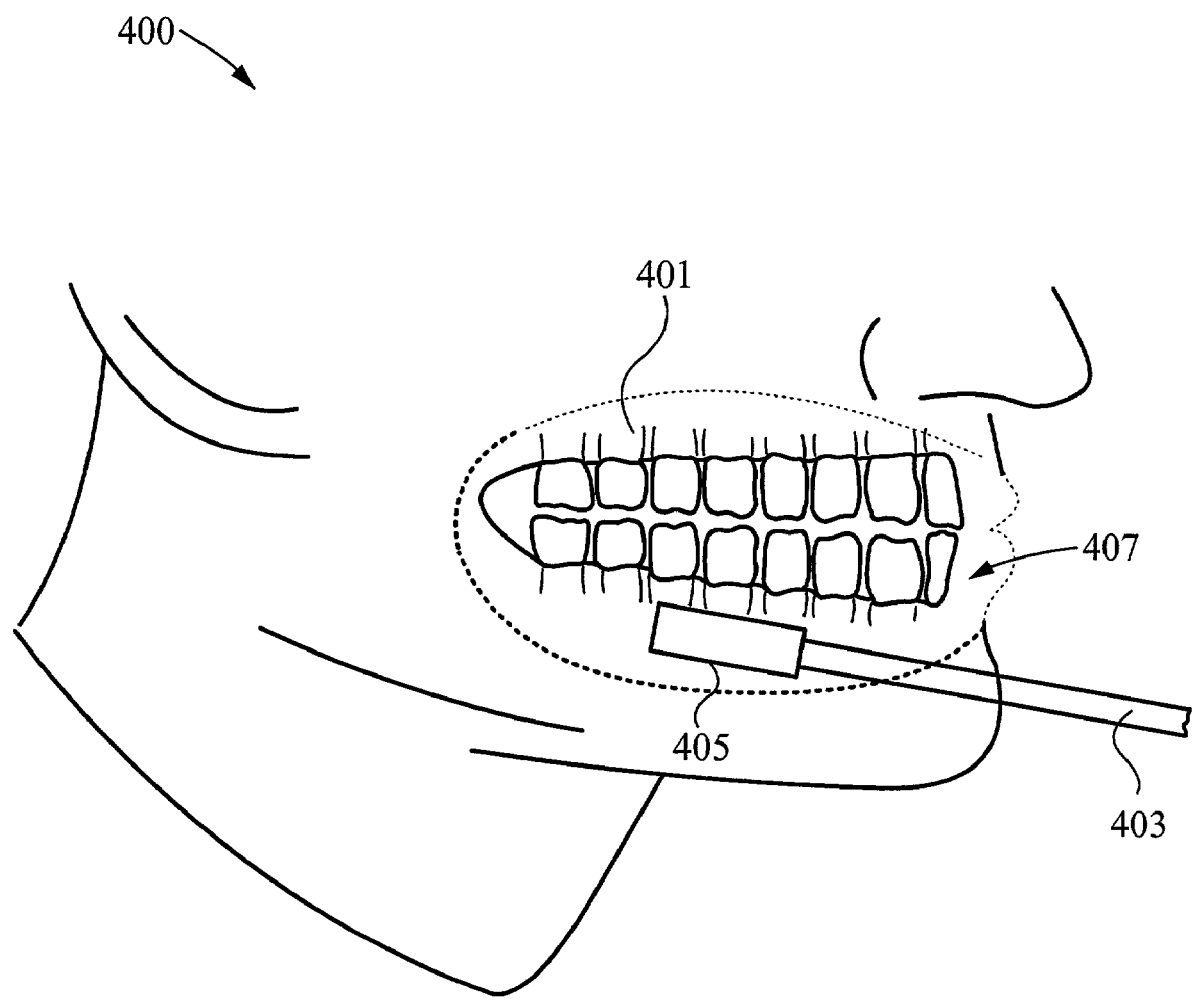
FIG. 4 illustrates applying laser radiation to the outer soft periodontal tissue from a delivery system, in accordance with the instant invention.

Now referring to FIG. 4, the laser radiation is preferably applied to the soft periodontal tissue 401 through a laser delivery system comprising an arm feature 403 and an applicator portion 405. Target pathogens within the oral cavity 407 can be stained with a staining agent which facilitates the absorption of the laser radiation by the pathogens. The arm feature 403 can house one or more optical fibers. Alternatively, the arm feature is a jointed arm with a series of focusing lens and/or mirrors for focusing a laser beam through the applicator 405 and onto the soft periodontal tissue 401. The choice of delivery system used depends in-part on the type of laser source used, because certain laser wavelengths are absorbed by typical optical fibers making such delivery systems less preferable.

In still further embodiments, the laser source is within the arm feature 403 or within the applicator portion 405. For example, the laser source is a high-powered laser diode that is housed within the arm feature 403 or applicator 405 and coupled with the appropriate optics to deliver laser radiation onto the soft periodontal tissue 401 and/or teeth dentin, cementum, bone plaque or any other infected periodontal tissue, as described preciously.

After the laser treatment of the soft periodontal tissue 401, as described above, the periodontal tissues within the oral cavity 407 can be tested for the presence of the target pathogens. The periodontal tissues within the oral cavity 407 can be tested for the presence of the target pathogens by growing a culture or by staining techniques, wherein topographically accessible pathogens are stained with a staining agent or pigment which stains for the presence of living pathogens. In the event that a number of pathogens are still present, then a second laser treatment can be administered to the soft periodontal tissue 401. Periodontal tissues within the oral cavity 407 can also be subjected to mechanical debridement procedures if necessary and/or antibiotic treatments prior to, during or after the laser treatment. Applying the laser treatment prior to mechanical or debridement procedures helps to decreases the concentration of pathogen or endotoxins in the debris generated form scaling, planing and secular debridement, and subsequently reduces the potential for the release of pathogen or endotoxins in to the patient's saliva and/or circulation system. However, the laser treatment described above, is preferentially used in place of aggressive mechanical tenements.

Figure 5:
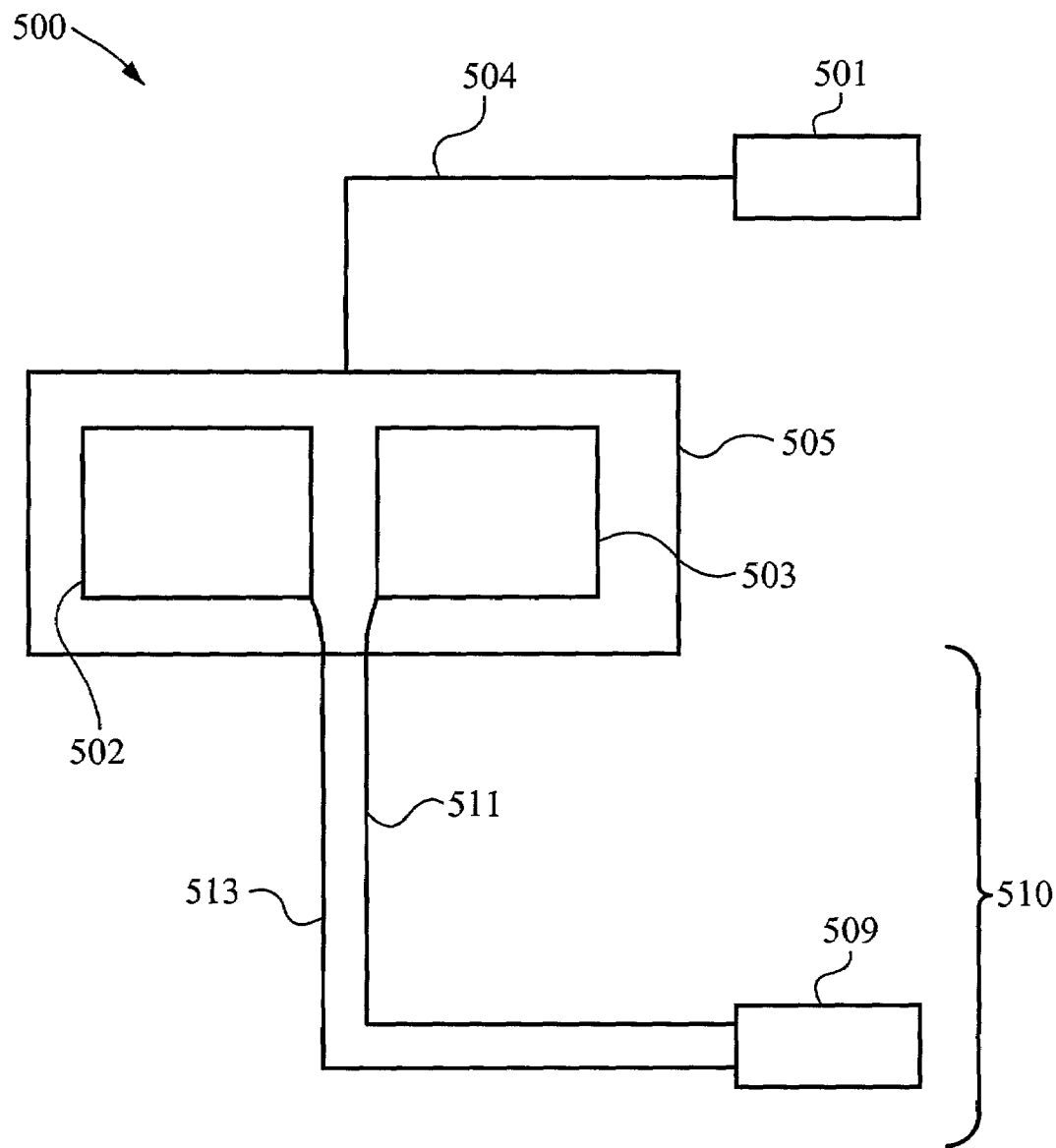
FIG. 5 is a schematic representation of the laser system for treating periodontal tissue with laser radiation, in accordance with the instant invention.

FIG. 5 shows a laser system 500 in accordance with the current invention. The laser system 500 preferably comprises a housing 505 for housing at least one laser source 502. The laser source 502 is preferably a Nd:YAG laser source. The laser source 502 is coupled to a power source 501 through the appropriate electrical connection 504 to provide power to the source 502. The laser system 500 also has a delivery system 510 for delivering laser light to a target tissue (not shown). In an embodiment of the invention delivery system 510 comprises an arm feature 513 for housing mirrors, lenses, optical fibers or any combination thereof. Alternatively, the delivery system 510 utilizes on or more optical fibers. Regardless of the optical used, the delivery system 510 is preferably configured for controllably directing laser radiation from the laser source 502 onto the target tissue. The delivery system 510 also preferably comprises an applicator 509. The applicator 509 is preferably configured to interface with the target tissue during laser treatment.

In accordance with an embodiment of the current invention, the laser system 500 also has a cooling source 503. The cooling source 503 is coupled to a cooling line 511 to deliver a cooling medium to the target tissue through the applicator 509. The cooling medium is a gas or a liquid or any combination thereof and is used to regulate the temperature of soft periodontal tissue before, during or after laser treatment.

Figure 6A:
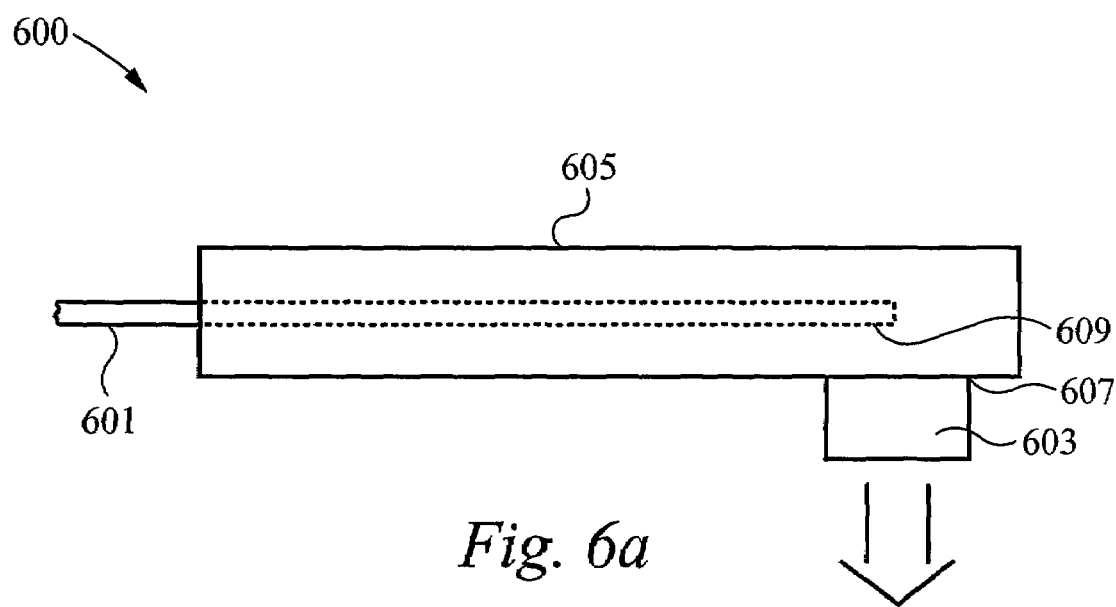
FIGS. 6a–b show views of an applicator portion having an optical fiber and guide member for treating periodontal tissue, in accordance with the current invention.
Figure 6B:
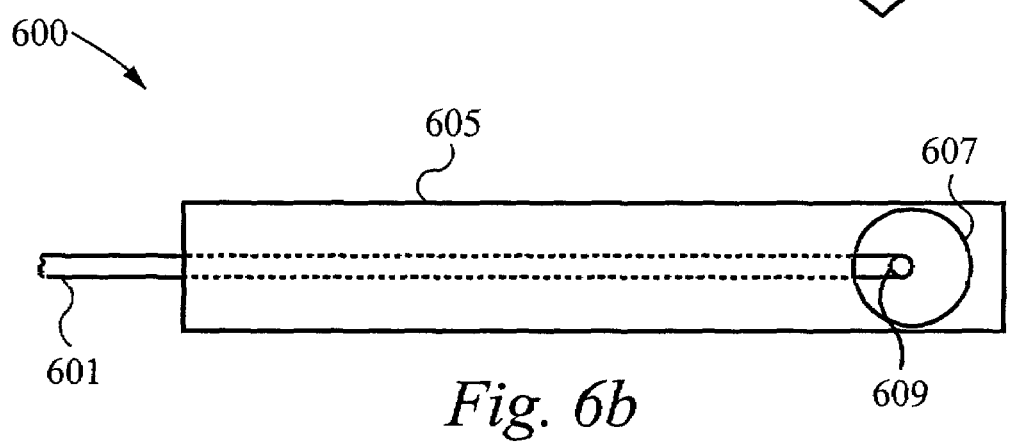

Referring now to FIGS. 6a–b, the applicator 600 of the instant invention preferably comprises an applicator housing 605 configured to be hand-held. An optical fiber 601 with a firing end 609 extends through the applicator housing 605 and is positioned to deliver laser radiation through an aperture 607 to a target tissue. The applicator 600 preferably has a guide member 603 that contacts soft periodontal tissues and regulates the distance between the firing end 609 and the target tissues during laser treatment. The guide member 603 is preferably formed from a soft resilient material, such as rubber, silicon, or latex and encircles the aperture 607. Preferably, the applicator 600 and or guide member 603 is capable of being sterilized or, alternatively, is configured to be disposable.

The current invention provides for the treatment of target pathogens within an oral cavity which can lead to the advancement of periodontal disease. The instant invention utilizes high-energy antiseptic laser pulses which are substantially transparent to periodontal tissues, but which are strongly absorbed by the target pathogens. The instant invention preferably eradicates the target pathogens without causing excessive systemic release of toxins and without requiring mechanical manipulation of the soft periodontal tissues. Further, the periodontal laser treatment of the instant invention can be administered any number of times as required to eradicate the target pathogens and the laser can be selected to target specific pathogens based on their respective absorption spectra.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications can be made in the embodiment chosen for illustration without departing from the spirit and scope of the invention. Specifically, while the present invention is preferably directed to treatment of periodontal tissues with pigmented gram (-) anaerobes, such as phorphyromonas gingivalis (Pg) and prevotella intermedia (Pi), the system for and method of the current invention can also be used to treat other target pathogens including fungi such as Histoplasma and Aspirgillus Niger.

What is claimed is:

1. A method of treating a pathogen within a periodontal pocket, the method comprising:
    a. testing for the presence of one or more pathogens within the periodontal pocket with a culture;
    b. selecting pulsed laser light with a wave length corresponding to an absorption spectrum of the pathogen; and
    c. irradiating a target tissue within an oral cavity with the pulsed laser light having an energy of 10 Joules/cm$^2$ or greater per pulse, wherein the pulsed laser light penetrates into the target tissue to a distance of 1.0 mm or greater and then eradicates at least a portion of the pathogen within the periodontal pocket of the target tissue.

2. The method of claim 1, wherein the pulsed laser light comprises a wavelength in a range of 580 to 1800 nanometers.

3. The method of claim 2, wherein the target tissue corresponds to a volume of soft periodontal tissue.

4. The method of claim 1, wherein the target tissue is selected from the group consisting of hard periodontal tissue and soft periodontal tissue.

5. The method of claim 4, further comprising debriding of the target tissue prior to the step of irradiating target tissue.

6. The method of claim 1, wherein the target tissue is irradiated with the pulsed laser light through an optical fiber.

7. The method of claim 6, wherein the optical fiber has a fiber diameter in a range of 0.05 to 3.0 mm.

8. The method of claim 1, wherein the target tissue is irradiated with a fluence of the pulsed laser light that is 350 Joule/cm$^2$ or greater.

9. The method of claim 1, wherein an area of the target tissue is irradiated with 2 Joules or more of pulsed laser light.

10. The method of claim 1, wherein an area of target tissue is irradiated with the pulsed laser light for less than 1.0 second.

11. The method of claim 1, wherein the one or more pathogens include a pigmented gram (-) anaerobe.

12. The method of claim 11, wherein the pigmented gram (-) anaerobe is selected from the group consisting of phorphyromonas gingivalis (Pg) and prevotella intermedia (Pi).

13. The method of claim 1, wherein one or more pathogens include a pigmented fungus.

14. The method of claim 13, wherein the pigmented fungus is a fungus selected from the group consisting of Histoplasma and Aspirgillus Niger.

15. The method of claim 1, further comprising staining a bacteria.

16. The method of claim 1, wherein a substantial portion of the one or more pathogens is eradicated.

17. A method of treating a periodontal pocket, the method comprising:
    a. generating a sequence of laser pulses at an absorption wavelength; and
    b. directing the laser pulses to a portion of periodontal tissue outside of the periodontal pocket, wherein the laser pulses penetrate through a volume of the periodontal tissue and then eradicates bacteria within the periodontal pocket.

18. The method of claim 17, further comprising applying a staining agent within the periodontal pocket, wherein the staining agent stains for the presence of living bacteria.

19. The method of claim 17, wherein the portion of periodontal tissue is selected from the group containing of dentin, cementum, bone and gum tissue.

20. The method of claim 19, wherein the laser pulses penetrate through the outer portion of periodontal tissue by a distance of 1.0 mm or more.

21. The method of claim 17, wherein the laser pulses are generated with a Nd:YAG laser.

22. The method of claim 17, wherein the laser pluses have energy concentrations of 17 Joules/cm$^2$ per pulse or greater.

23. The method of claim 17, wherein the laser pulses are directed to the portion of periodontal tissue from an optical fiber.

24. The method of claim 23, wherein the optical fiber has a fiber diameter in a range of 0.5 to 3.0 mm.

25. The method of claim 17, wherein the bacteria is a pigmented gram (-) anaerobe.

26. The method of claim 17, wherein the pigmented gram (-) anaerobe is selected from the group consisting of phorphyromonas gingivalis (Pg), prevotella intermedia (Pi) and a pigment fungi.

27. The method of claim 17, wherein directing the laser pulses to the portion of periodontal tissue also eradicates a portion of a pigmented fungus within the periodontal tissue.

28. The method of claim 27, wherein the pigmented fungus is a fungus selected from the group consisting of Histoplasma and Aspirgillus Niger.

29. A method of treating a pathogen within a periodontal pocket, the method comprising:
    a. selecting pulsed laser light with a wave length corresponding to an absorption spectrum of the pathogen; and
    b. irradiating a target tissue within the oral cavity with the pulsed laser light having an energy of 10 Joules/cm$^2$ or greater per pulse, wherein the pulsed laser light penetrates into the target tissue to a distance of 1.0 mm or greater and then eradicates at least a portion of the pathogen within the periodontal pocket.

30. The method of claim 29, further comprising testing for the presence of the pathogen within the periodontal pocket.

* * * * *